(12) United States Patent
Ly

(10) Patent No.: US 11,793,600 B2
(45) Date of Patent: Oct. 24, 2023

(54) RETRACTABLE STYLET DECLOG MECHANISM

(71) Applicant: GYRUS ACMI, INC., Southborough, MA (US)

(72) Inventor: Canh S Ly, Cordova, TN (US)

(73) Assignee: Gyrus ACMI, Inc., Westborough, MA (US)

(*) Notice: Subject to any disclaimer, the term of this patent is extended or adjusted under 35 U.S.C. 154(b) by 536 days.

(21) Appl. No.: 17/031,352

(22) Filed: Sep. 24, 2020

(65) Prior Publication Data

US 2021/0100634 A1 Apr. 8, 2021

Related U.S. Application Data

(60) Provisional application No. 62/994,025, filed on Mar. 24, 2020, provisional application No. 62/909,975, filed on Oct. 3, 2019.

(51) Int. Cl.
*A61B 17/3207* (2006.01)
*A61B 90/70* (2016.01)
*A61B 17/00* (2006.01)

(52) U.S. Cl.
CPC ...... *A61B 90/70* (2016.02); *A61B 17/320783* (2013.01); *A61B 2017/00424* (2013.01); *A61B 2217/005* (2013.01); *A61B 2217/007* (2013.01)

(58) Field of Classification Search
CPC ...... A61B 17/32002; A61B 17/320783; A61B 90/70; A61B 2090/701
See application file for complete search history.

(56) References Cited

U.S. PATENT DOCUMENTS

| | | | |
|---|---|---|---|
| 6,183,433 B1 | 2/2001 | Bays | |
| 7,854,728 B2* | 12/2010 | Boyle, Jr. | A61M 16/0463 15/104.16 |
| 9,694,119 B2* | 7/2017 | Cheng | A61B 17/32002 |

* cited by examiner

*Primary Examiner* — Deanna K Hall
(74) *Attorney, Agent, or Firm* — Schwegman Lundberg & Woessner, P.A.

(57) ABSTRACT

A debrider or other medical device can include an extendable and retractable stylet to ream or unclog a working lumen, a distal portal, or the like. The device can include an elongate tubular body with a proximal and a distal portion. A working lumen can extend from a proximal working lumen portal at the proximal portion of the tubular body to a distal working lumen portal at the distal portion of the tubular body. The device can also include an auxiliary passage, interconnected to the working lumen of the tubular body at an auxiliary lumen portal located between the proximal working lumen portal and the distal working lumen portal. A spoolable or otherwise extendable and retractable stylet can include at least a portion of the stylet being extendable into the working lumen and toward the distal working lumen portal via the auxiliary lumen portal, and the stylet being retractable from the working lumen via the auxiliary lumen portal.

17 Claims, 10 Drawing Sheets ent Application Ser. No. 62/994,025, filed on Mar. 24, 2020; the contents of which are incorporated by reference herein in their entireties.

TECHNICAL FIELD

The present disclosure relates generally to a medical device with a retractable stylet for declogging tissue from a target area and a method for operating the medical device during medical surgical procedure.

BACKGROUND

A debrider is a type of endoscopic medical device that can be used to remove tissue upon being inserted into a human patient during medical procedures.

Debriders may be used for ear, nose, and throat (ENT) procedures and include components to remove tissue from target areas. Bits of tissue being removed can clog an evacuation channel through which such tissue bits are removed under suction. One approach to clearing a clog is to use positive air pressure instead of suction. However, it may still be difficult to provide adequate suction to fully clear the clog.

U.S. Pat. No. 6,183,433 to F. Barry Bays describes an approach involving a surgical suction cutting instrument, which can be either difficult to use in practice or inadequate to fully clear a clog quickly.

SUMMARY

Thus, the present inventors have recognized a need for a debrider declog mechanism to efficiently help physically remove tissue. This document describes a retractable stylet declog mechanism. For example, a medical device can be configured to be at least partially inserted into a human patient. The medical device can include an elongate tubular body. The elongate tubular body can include a proximal portion and a distal portion. The elongate tubular body can define a working lumen extending from a proximal working lumen portal at the proximal portion to a distal working lumen portal at the distal portion. An auxiliary passage can be interconnected to the working lumen of the tubular body, such as at an auxiliary lumen portal. The auxiliary lumen portal can be located between the proximal working lumen portal and the distal working lumen portal. A stylet can include at least a portion of the stylet. The stylet can extend into the working lumen and toward the distal working lumen portal via the auxiliary lumen portal. The stylet can retract from the working lumen such as via the auxiliary lumen portal.

This document also describes a method of medical therapy of a human patient. The method can include inserting a distal portion of a tubular body into the patient. The tubular body can include a working lumen. At least a first portion of a stylet can be extended from a chamber into a region of the working lumen such as via an auxiliary lumen portal toward the distal working lumen portal. At least a portion of the stylet can be retracted into the chamber from the working lumen such as via the auxiliary lumen.

DETAILED DESCRIPTION

This document describes, among other things, a stylet component that may be used as a component of a medical device, such as medical shaver or debrider, such as during an endoscopic surgical procedure. During surgical debridement, a practitioner can use a debrider to remove dead, damaged, infected, or other unwanted tissue. Using a debrider to remove the tissue can be quicker and can provide better access and more control than cutting away the tissue with a scalpel.

The medical device described herein focuses on an illustrative example that can include a debrider, such as can include an elongated tubular body with a proximal portion and a distal portion. A working lumen can extend from a proximal working lumen portal at the proximal portion of the elongated tubular body to a distal working lumen portal at the distal portion of the tubular body. An auxiliary passage can be interconnected to the working lumen, such as with an auxiliary lumen portal that can be located between the proximal working lumen portal and the distal working lumen portal. A stylet can be extended from or retracted into a chamber from the working lumen such as via the auxiliary lumen portal.

The stylet can utilize physical force to clear tissue clogs in the distal working lumen portal without requiring applying air pressure to the working lumen to clear tissue clogs during surgery. The stylet may also allow the medical device to remain inside the patient during surgery when the stylet is needed to declog and remove tissue occluding the working lumen.

Figure 1:
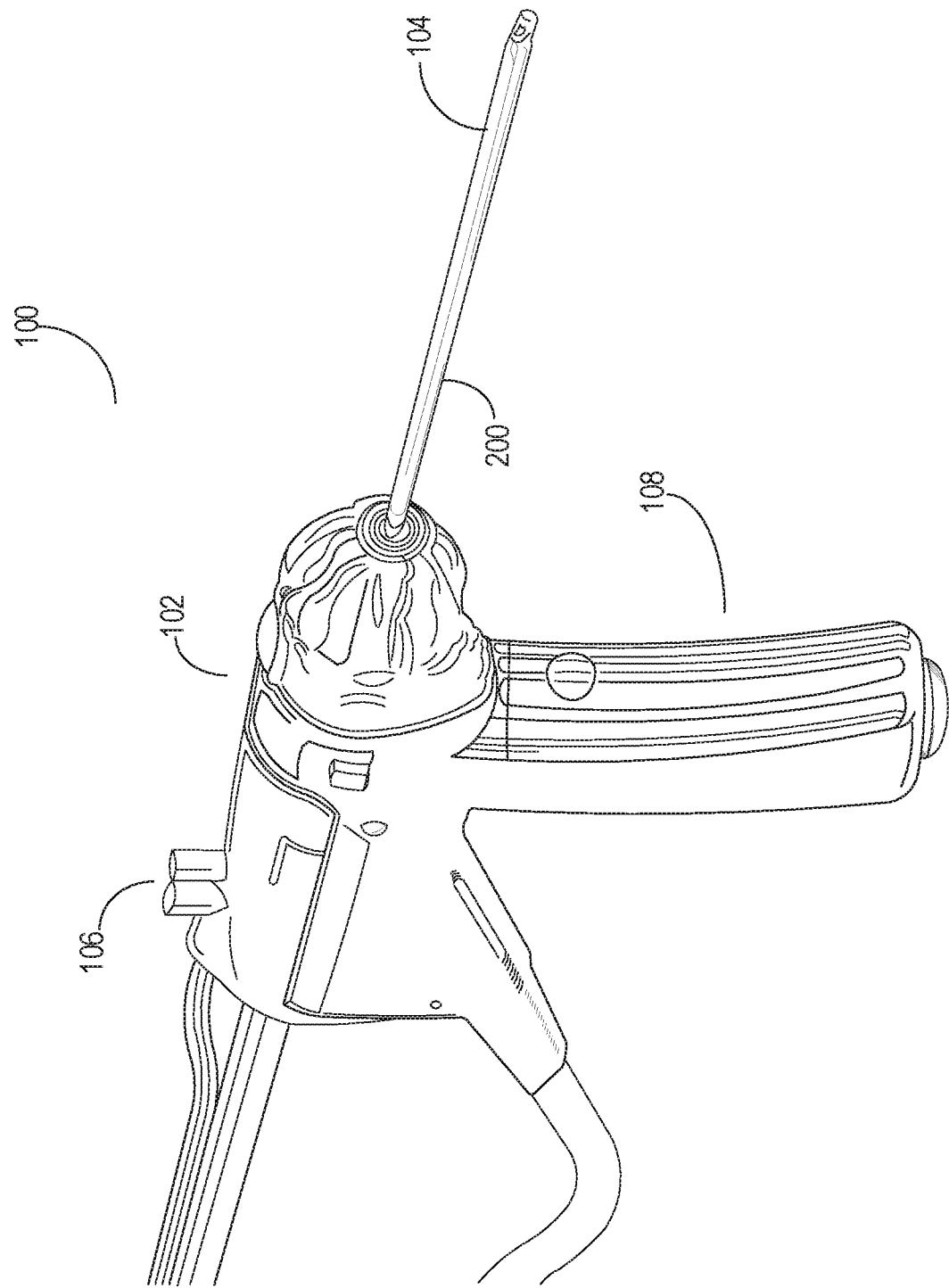
FIG. 1 is an example of a medical device.

FIG. 1 is an example of a medical device. For purposes of illustration, a debrider is described as the present medical device. However, any endoscopic or other medical device having a working lumen may benefit from using the present techniques. In FIG. 1, a debrider 100 can be shaped and sized to be handheld by a medical practitioner during use (e.g., a microdebrider). However, the debrider 100 need not be handheld by a medical practitioner during use. For example, the debrider 100 can be controlled robotically. Many of the features and components of the debrider 100 can be scaled up or down as needed, depending on the application of the debrider 100. The debrider 100 may include a proximal portion 102 and an elongate tubular body with a distal portion 104. For example, the elongate tubular body of the debrider 100 may be cylindrical, polygonal, hexagonal, or any other shape suitable for use such as described herein.

The proximal portion 102 can include a handle, such as can be shaped to be gripped by a practitioner during use. The handle can include one or more user controls, such as a power button, and one or more connections such as to electrical power, suction, an irrigation hub 106, which can be used to provide irrigation via irrigation tubing, or the like. The proximal portion 102 may also include a proximal hub chamber 108, such as which can house the extendable and retractable stylet when retracted. The debrider 100 can include a distal portion 104 such as extending distally from the proximal portion 102.

Figure 2:
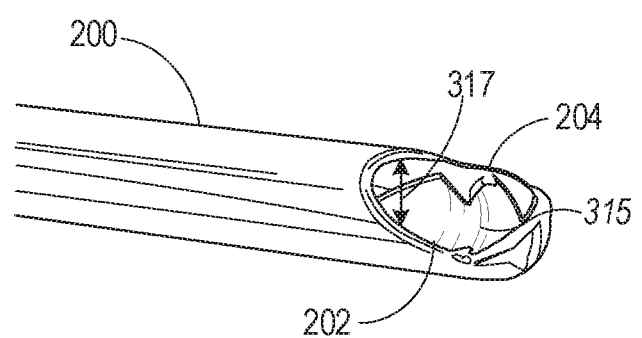
FIG. 2 is an enlarged cross-sectional view of a distal working lumen portal at the distal portion of the tubular body of the medical device.

FIG. 2 illustrates an enlarged cross-sectional view of a distal working lumen portal 202 at the distal portion of the tubular body 200 of the debrider or another medical device. The elongate tubular body 200 may be in any polygonal or tubular shape configuration including, but not limited to hollow, tube-like, cylindrical, round, or globular. The distal working lumen portal 202 can include one or more instruments, such as cutting element 204 (e.g., one or more blades or a burr), that may be positioned or exposed at a distal working lumen portal 202 of the debrider 100. A distal cutout outer opening 317 can expose the cutting element that can be provided by a rotating edge of a distal cutout inner opening 315 of the distal cutout outer opening 317.

Figure 3:
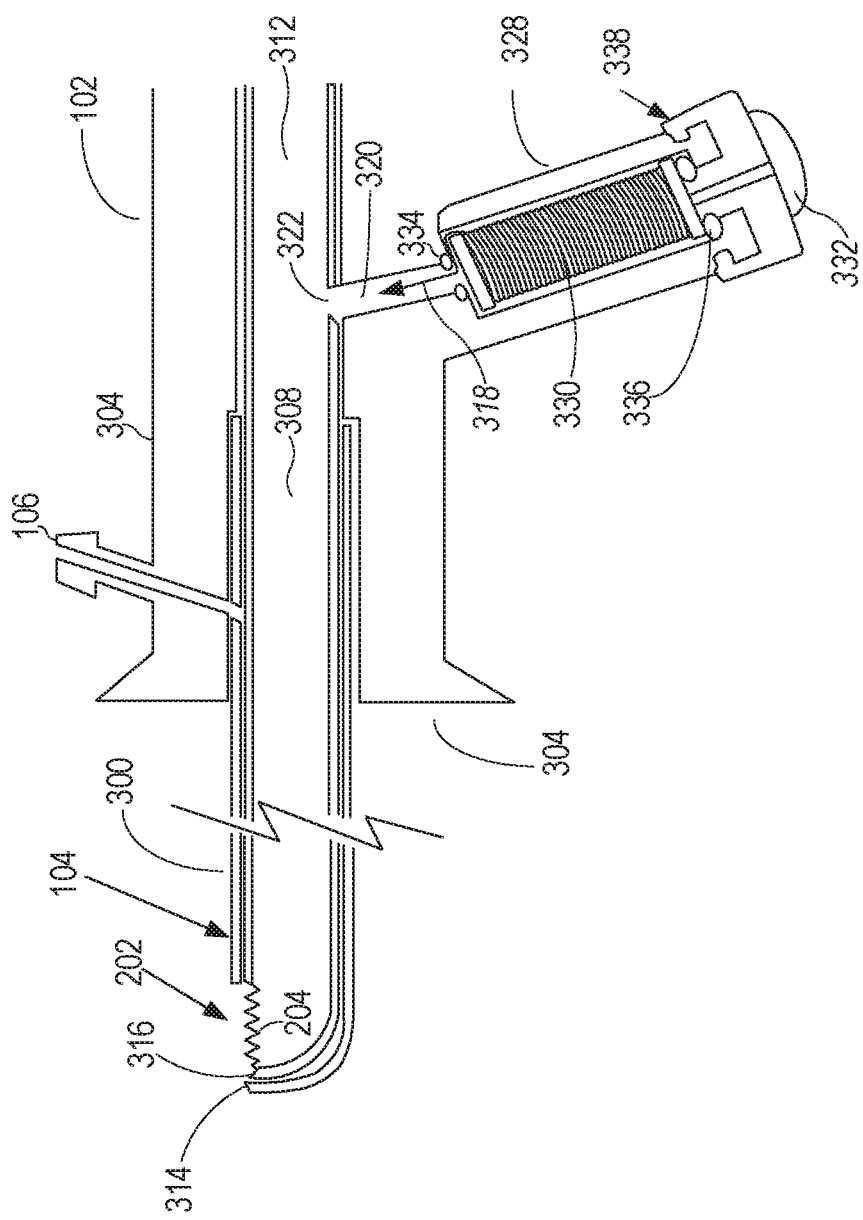
FIG. 3 is a side section view of the medical device with a stylet partially retracted into a mandrel.

FIG. 3 depicts a side section view of the debrider or another medical device with a stylet partially retracted onto a mandrel. The proximal portion 102 may include an irrigation hub 106, an outer casing 304, a working lumen 308, the distal working lumen portal 202, a proximal working lumen portal 312, an outer tubular member 314 including the distal cutout outer opening 317 and an inner tubular member 316 including the distal cutout inner opening 315. The distal working lumen portal 202 can be formed by the alignment of the distal cutout outer opening 317 with the distal cutout inner opening 315, such as during a particular phase or orientation of the rotation of the inner tubular member 316 with respect to the outer tubular member 314.

The irrigation hub 106 may be connected to the outer casing 304. The irrigation hub 106 may be positioned at any suitable desired position relative to the proximal portion 102 or to the distal portion 104, or both. The outer casing 304 may provide protection and structural support to one or more internal components, such as described herein. The irrigation hub 106 may include tubing, such as can be configured to receive and provide a fluid or flowable irrigation solution such as to help remove one or more of tissue, pathogens, or other biological debris such as may be created or ingested or aspirated while operating the debrider 100. An irrigation passage may extend from the irrigation hub 106 toward the distal portion 104 of the debrider 100.

The distal portion 104 can include an outer tubular member 314 with the distal cutout outer opening 317. Within the outer tubular member 314, there can be an inner tubular member 316 such as may include the distal cutout inner opening 315, which can align with the distal cutout outer opening 317 at a particular rotational orientation of the rotating inner tubular member 316. The inner tubular member 316 can be actuated to rotate with respect to the static outer tubular member 314 in response to motion imparted by an actuator that may be included within the debrider 100 outer casing 304 at the proximal portion 102.

The inner tubular member 316 may be coaxial with and rotatable with respect to the outer tubular member 314. The inner tubular member 316 may also oscillate or reciprocate in an axial direction with respect to the outer tubular member 314. For example, when the inner tubular member 316 oscillates, during rotation in a first direction (e.g. clockwise direction or counterclockwise direction), the inner tubular member 316 may stop after a predetermined number of revolutions, and then reactivate rotation in an opposite direction (e.g. clockwise or counterclockwise direction). When the inner tubular member 316 reciprocates in an axial direction the stylet 318 reaches the inner tubular member 316 avoiding being stuck within the tubular body 300. The distal portion 104 can include one or more instruments, such as cutting element 204 (e.g. blade(s) or a burr), that may form (or be located adjacent to) the distal working lumen portal 202 of the debrider 100. The cutting element 204 can include a sharpened blade edge of the distal cutout inner opening 315. The outer tubular member 314 can expose the cutting element 204 as the cutting element 204 (e.g., the distal cutout inner opening 315) rotates as part of the rotating inner tubular member 316.

The working lumen 308 may extend between from the proximal working lumen portal 312 at the proximal portion 102 of the tubular body 300 to the distal working lumen portal 202 at the distal portion 104 of the tubular body 300. The working lumen 308 can include a lateral region that can interface with an auxiliary lumen portal 322, such as to define an inter-axial lateral angle therebetween that can be oriented toward the distal end of the tubular body 300. The working lumen 308 may extend toward the distal portion 104 of the tubular body 300. The working lumen 308 may open to an external region such as at a distal working lumen portal 202, at a proximal working lumen portal 312, or at both.

The distal working lumen portal 202 may be located at the distal portion 104 of the tubular body 300 and may optionally have an opening that can be sized to accommodate the width and height of a stylet 318. The stylet 318 can be extendable and retractable. The stylet 318 can be user-extended into the working lumen 308, such as by accessing through the auxiliary lumen portal 322 located between the proximal working lumen portal 312 and the distal working lumen portal 202. An auxiliary passage 320 can include a pathway interconnected to the working lumen 308 of the tubular body 300 at the auxiliary lumen portal 322. The auxiliary lumen portal 322 may include a rotatable opening in the inner tubular member 316 that is capable of being rotatably aligned with a static opening in the outer tubular member 314.

The size and shape of the auxiliary passage 320 may vary but can include a shape, width, and height that can accommodate the shape, width, and height of the stylet 318 such as can be translated within the auxiliary passage 320. The stylet 318 can include a flexible or bendable polymer or metallic rod, wire, or another elongate member, such as to permit at least a portion of the stylet 318 to be user-extendable into the working lumen 308 and toward the distal working lumen portal 202 via the auxiliary lumen portal 322.

As shown in FIG. 3, a proximal hub chamber 328 may be coupled to the auxiliary lumen portal 322. The proximal hub chamber 328 can be configured to house and spool at least a portion of the stylet 318 when that portion is retracted from the working lumen 308 into the proximal hub chamber 328. The proximal hub chamber 328 may house or contain a rotatable mandrel 330 such as can be configured to spool and unspool at least a portion of the stylet 318. A seal 336 can be located between the proximal hub chamber 328 and a cap housing 338, such as about a shaft extending from a user-accessible knob 332 to the mandrel 330. A seal 334 may be located between the working lumen 308 and the proximal hub chamber 328. At least a portion of the stylet 318 may be spooled in the proximal hub chamber 328, such as wrapped around the rotatable mandrel 330 such as to inhibit or prevent tangles of loops of the stylet 318. Such spooling can be actuated and controlled by the user, such as by using the user-accessible knob 332 coupled by a shaft to the mandrel 330. Rotation of the knob 332 can cause rotation of the mandrel 330 in a first direction. This can unspool at least a portion the stylet 318 such as to permit extension into the working lumen 308 via the auxiliary lumen portal 322.

Rotation of the mandrel 330 can also occur in a second direction. This can re-spool at least a portion of the stylet 318. Thus, via the user-accessible knob 332, the mandrel 330 may be configured to rotate in a first direction to unspool the stylet 318 for extending at least a portion of the stylet 318 into the working lumen 308 and to rotate in an opposite second direction to spool at least a portion of the stylet 318 for retracting at least a portion of the stylet 318 into the proximal hub chamber 328 from the working lumen 308. During retraction of the stylet 318, a distal portion of the stylet 318 can be left positioned within the auxiliary passage 320. The auxiliary lumen portal 322 can be an opening that can be located in between the auxiliary passage 320 and the working lumen 308 and that may be sized and shaped to accommodate the width and height or other cross-sectional profile dimension of the extendable and retractable stylet 318.

Figure 4:
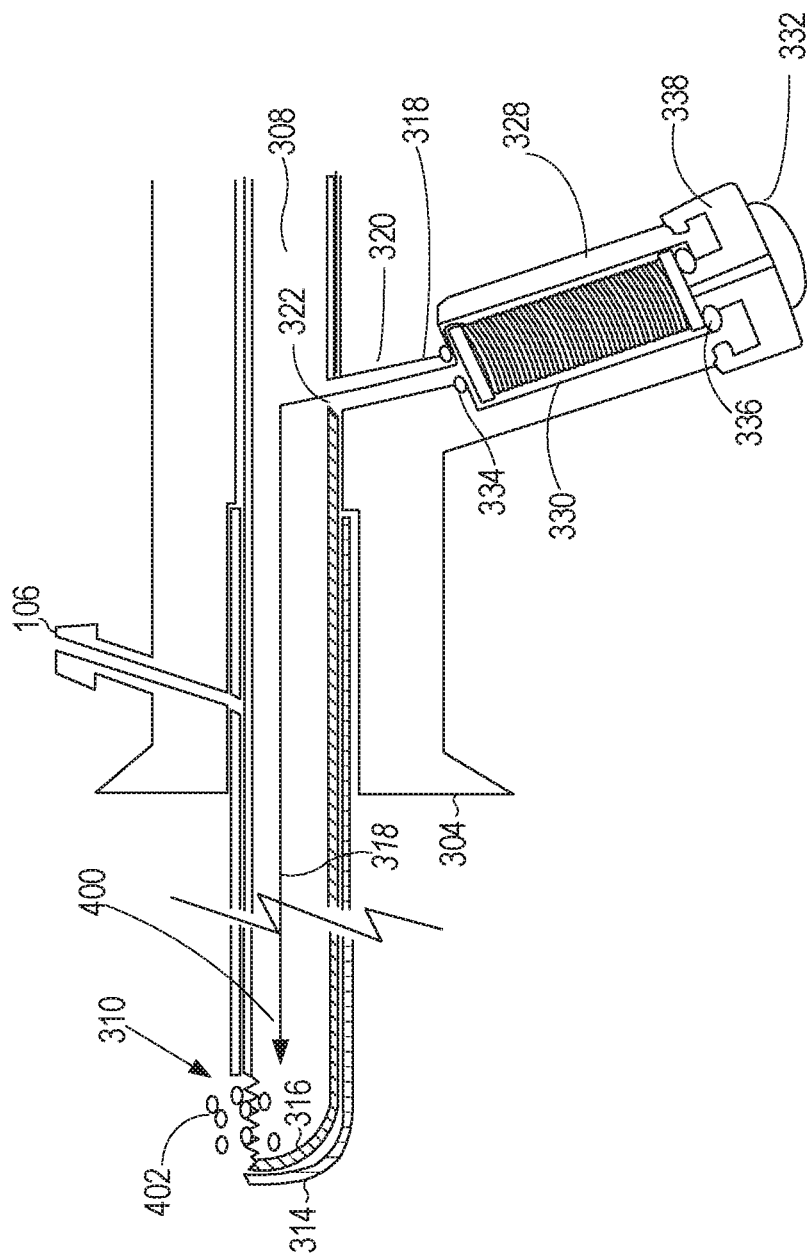
FIG. 4 is a side section view of the medical device with the stylet extended into the working lumen and towards the distal working lumen portal.

FIG. 4 is a side section view of portions of the medical device with a portion of the stylet 318 extended into the working lumen 308 and toward the distal working lumen portal 202. When turning the knob 332 in a direction such as to extend and unspool the stylet 318, a distal portion 400 of the stylet 318 can extend from the chamber 328 through the auxiliary passage 320 and through the auxiliary lumen portal 322 and through the working lumen 308 toward the distal working lumen portal 202. The user of the debrider 100 is able to extend at least a portion of the stylet 318 from the chamber 328 by turning the knob 332 and rotating the mandrel 330 so as to extend a portion of the stylet 318 through the working lumen 308 and into the inner tubular member 316 and (optionally) out through the distal working lumen portal 202 such as via the distal cutout inner opening 315 and via the distal cutout outer opening 317.

Once the stylet 318 is extended to or through the distal working lumen portal 202, it can physically declog or remove bits of physical tissue 402 that may have been occluding a region of the working lumen 308 near or at the distal portion 104 or the distal working lumen portal 202. Such debrided bits of physical tissue 402 may include any organic biological tissue such as can include nasal tissue, vocal cord tissue, fibroids, polyps, or dead organic tissue. Declogging the tissue 402 at or via the distal working lumen portal 202 may also include one or more of suctioning, irrigation, or positive air or fluid pressure via the working lumen 308, such as together with reaming of the working lumen 308 using the stylet 318. For example, irrigation may be provided from the irrigation hub 106 while the stylet 318 interacts with and removes one or more bits of the physical tissue 402.

Figure 5:
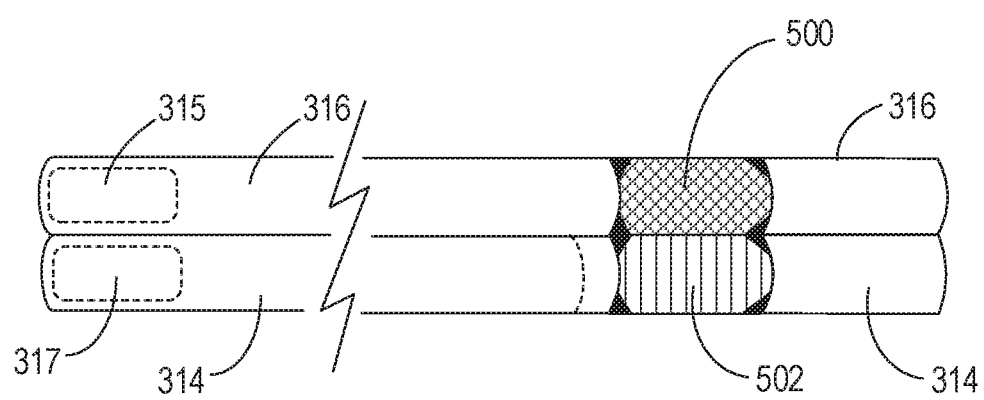
FIG. 5 is a side perspective section view of the access openings of the inner tubular member and outer tubular member of the medical device.

FIG. 5 is a side perspective section view showing the access openings 500, 502 of the respective inner tubular member 316 and outer tubular member 314 of the medical device, when such cylinders 316, 314 are arranged side-by-side (as shown in FIG. 5) instead of in their normal arrangement in which the inner tubular member 316 is located coaxially within the outer tubular member 314. The access opening 500 of the inner tubular member 316 and the access opening 502 of the outer tubular member 314 may be sized, shaped, or otherwise configured at a width, height, and shape that can accommodate for passage the width, height, and shape of at least a portion of the stylet 318. The access opening 500 may be configured to be aligned with or form part of the auxiliary lumen portal 322 at a specified rotational orientation of the inner tubular member 316, or may be aligned with the auxiliary lumen portal 322 when extending the stylet 318, or a portion of the stylet 318, from the chamber 328 or the auxiliary passage 320 into the working lumen 308 such as via the auxiliary lumen portal 322 toward the distal working lumen portal 202. The access opening 500 in the inner tubular member 316 may also be aligned with the auxiliary lumen portal 322 when retracting the stylet 318, or a portion of the stylet 318, back into the chamber 328 from the working lumen 308 via the auxiliary lumen portal 322.

The access opening 502 of the outer tubular member 314 may be configured to be aligned with the auxiliary lumen portal 322 at a specified rotation orientation of the inner tubular member 316 or may be aligned with the auxiliary lumen portal 322 when extending the stylet 318, or a portion of the stylet 318, from the chamber 328 into the region of the working lumen 308 via the auxiliary lumen portal 322 toward the distal working lumen portal 202. Furthermore, any access opening 502 in the outer tubular member 502 may also be aligned with the auxiliary lumen portal 322 when retracting the stylet 318, or a portion of the stylet 318, back into the chamber 328 from the region of the working lumen 308 via the auxiliary lumen portal 322 toward the proximal working lumen portal 312. As explained, no access opening 502 need be present in an example in which a proximal end of the outer tubular member 314 terminates at a more distal location than the auxiliary lumen portal 322. As explained, the distal cutout inner opening 315 and the distal cutout outer opening 317 may also be rotationally aligned to each other, such as when (1) the access openings 500, 502 of the respective inner tubular member 316 and outer tubular member 314 are rotationally aligned with each other and with the auxiliary passage 320 to establish a passageway via the auxiliary lumen portal 322. In FIG. 5, the distal cutout inner opening 315 and the distal cutout outer opening 317 are shown in dashed lines to indicate rotational alignment on the backside of their respective cylinders when the access openings 500, 502 are rotationally aligned on the frontside of their respective cylinders. However, this is not required. Both sets of openings 315, 317 and 500, 502 can be located on the same side of their respective cylinders or offset by an amount other than 180 degrees. By rotationally aligning the openings 315, 317 when the openings 500, 502 are also rotationally aligned, the stylet 318 can be extended both into the working lumen and (optionally) out of the openings 315, 317.

For extending the stylet 318, the inner tubular member 316 may include the access opening 500 such as may be rotatable to be aligned with or form part of the pathway provided by the auxiliary lumen portal 322 at a specified rotational orientation of the inner tubular member 316. For instance, the rotating access opening 500 in the inner tubular member 316 may be aligned with a static access opening 502 in the outer tubular member 314 to establish or align with the auxiliary lumen portal 322. Such alignment can permit extending a portion of the stylet 318, such as from the chamber 328 into the working lumen 308 via the auxiliary lumen portal 322, such as in a manner that is angled or otherwise directed toward the distal working lumen portal 202. Furthermore, the access opening 500 in the inner tubular member 316 may also be aligned with or form part of the auxiliary lumen portal 322 for retracting a portion of the stylet 318 back into the chamber 328 from the working lumen 308. In another example, such as shown in FIG. 4, the static outer tubular member 314 may terminate at a more distal location than the auxiliary lumen portal 322, such that no static access opening 502 in the outer tubular member 314 is required since the auxiliary passage 320 can directly access the working lumen 308 via the rotatable access opening 500 in the inner tubular member 202.

The specified rotational orientation of the inner tubular member 316 may be with respect to the static outer tubular member 314, with rotation therebetween possible as the debrider 100 is being operated by a user. The auxiliary lumen portal 322 may provide the access opening 500 via a lateral wall of the working lumen 308 such as provided by the inner tubular member 316. The auxiliary lumen portal 322 can permit the stylet 318 to access the working lumen 308 via the auxiliary lumen portal 322, such as at a lateral angle that can orient the distal end of the stylet 318 toward the distal portion 104 of the tubular body provided by the inner tubular member 316. The distal cutout inner opening 315 and the distal cutout outer opening 317 may also be rotationally aligned to each other, such as when (1) the access openings 500, 502 of the respective inner tubular member 316 and outer tubular member 314 are rotationally aligned with each other and with the auxiliary passage 320 to establish a passageway via the auxiliary lumen portal 322, or (2) the access opening 500 of the inner tubular member 316 is rotationally aligned with the auxiliary passage 320 (such as in an example in which the proximal portion of the outer tubular member 314 terminates at a more distal location than the auxiliary passage 320, such as shown in FIG. 4.

Figure 6:
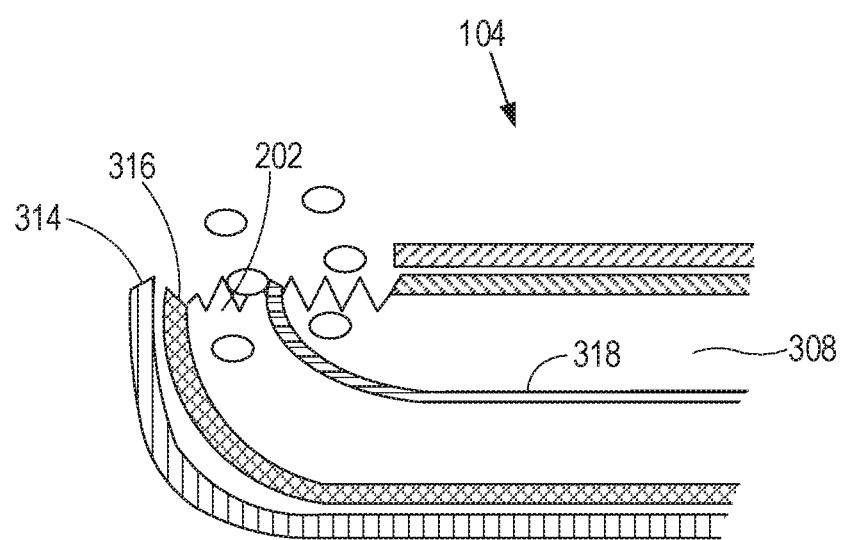
FIG. 6 is a side section view of the aligned access openings of the outer tubular member, and inner tubular member of FIG. 5 with the distal inner tubular member cutout blade opening and distal outer tubular member cutout blading opening.

FIG. 6 is a side section view of the distal portion of the outer tubular member 314 and the distal portion of the inner tubular member 316, with the distal cutout outer opening 317 aligned with the distal cutout inner opening 315. FIG. 6 illustrates an enlarged view as the stylet 318 is extended into the working lumen 308 and toward the distal working lumen portal 202, which can be open when the distal cutout outer opening 317 is aligned with the distal cutout inner opening 315. The stylet 318 can be introduced into the working lumen 308 via the auxiliary lumen portal 322, which can be open when the access openings 500 and 502 of the respective inner tubular member 324 and outer tubular member 326 are aligned at a specified rotational orientation of the inner tubular member 324 with the auxiliary passage 320. As further shown, the distal outer tubular member blade opening 314 and distal inner tubular member blade opening 316 may be aligned to open laterally toward physical tissue to be debrided.

Figure 7:
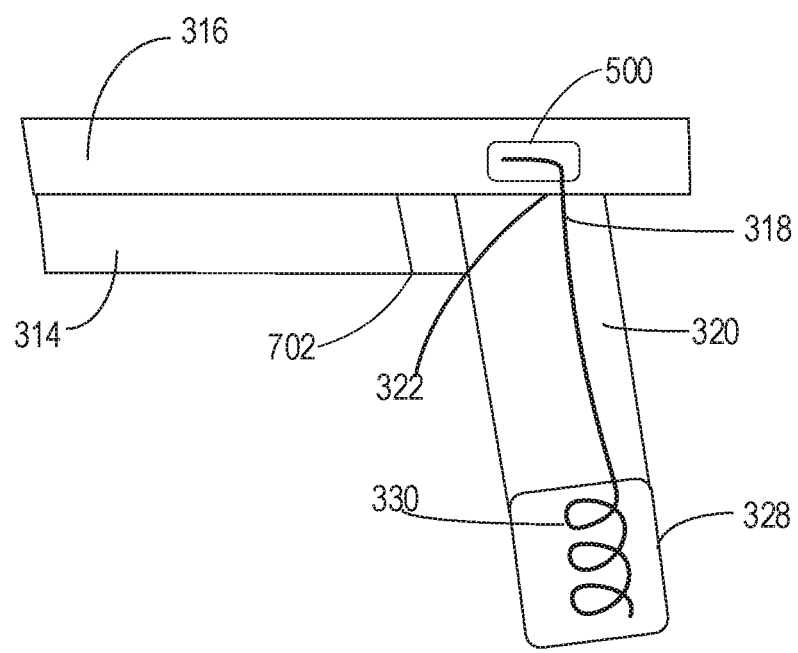
FIG. 7 is an enlarged side perspective section view of the auxiliary working lumen portal and proximal working lumen portal with the stylet being extendable from the chamber through an auxiliary passage into the auxiliary working lumen portal.

FIG. 7 is a side perspective section view showing the access opening 500 of the respective inner tubular member 316 and outer tubular member 314 of the medical device, when such cylinders 316, 314 are arranged side-by-side (as shown in FIG. 5) instead of in their normal arrangement in which the inner tubular member 316 is located coaxially within the outer tubular member 314. Unlike the example shown in FIG. 5, in FIG. 7, the outer tubular member 314 can terminate at an outer tubular member proximal end 702 that is more distal than the auxiliary passage 320.

In FIG. 7, the stylet 318 can be extendable from the chamber 328 via the auxiliary passage 320 and the auxiliary working lumen portal 322, which can be formed when the access opening 500 is rotationally aligned with the auxiliary passage 320. Because proximal end 702 of the outer tubular member 314 terminates at a more distal location than the auxiliary passage 320, the stylet 318 need not extend through any access opening 502 in the outer tubular member 314, in this example. Instead, the access opening 500 is aligned at a specified rotational orientation of the inner tubular member 316 with the auxiliary passage 320. The stylet 318 is shown as being extended and unspooled from the mandrel 330 within the chamber 308 and through the auxiliary passage 320.

Figure 8:
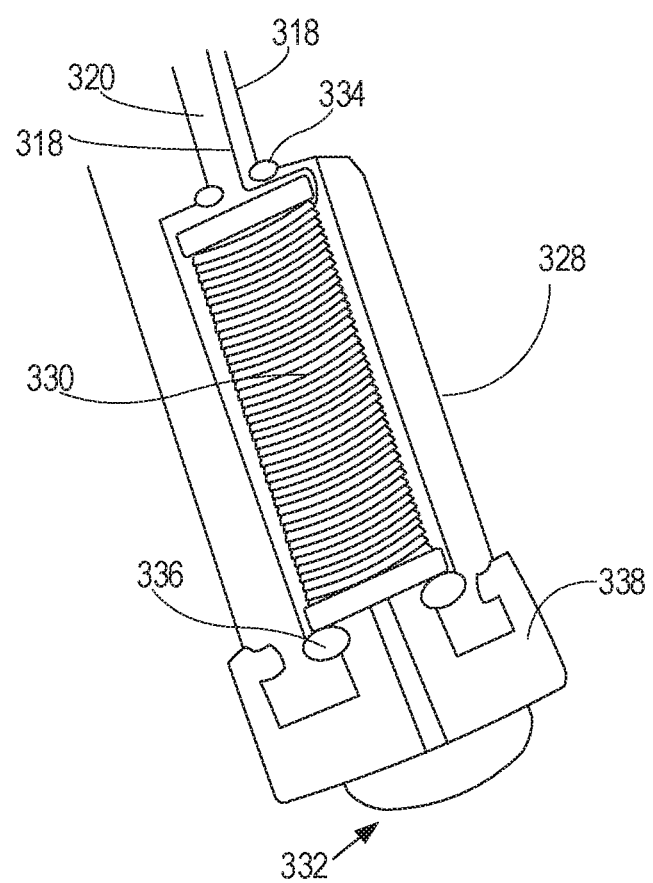
FIG. 8 is an enlarged view of a proximal hub chamber of the medical device.

FIG. 8 is an enlarged view of a proximal hub chamber 328 of the medical device. As shown, the proximal hub chamber 328 is fully assembled, with the stylet 318 in the retracted position, and coupled to the tubular body at the proximal portion 102 of the debrider 100. The proximal hub chamber 328 may house or contain a mandrel 330. The mandrel 330 can be configured to spool at least a portion of the stylet 318. A seal 336 can be located between the proximal hub chamber 328 and a user-accessible knob 332 and a cap housing 338. When a clog of physical tissue is encountered at or near the distal working lumen portal 202, such as within the working lumen 308, the clog can be reamed by the stylet 318 by the user turning the knob 332. This can affect rotating of the mandrel 330 in a direction to unspool the stylet 318. Such unspooling can extend at least a portion of the stylet 318 into the working lumen 308 and toward the distal working lumen portal 202. Once the stylet 318 reaches the clog, either within the working lumen, at the distal working lumen portal 202, or even slightly beyond, the stylet 318 may clear the clog of physical tissue by applying a translational mechanical force for reaming the clog. Once the clog of physical tissue is cleared, the knob 332 may by turned in an opposite direction. This can retract and spool at least a portion of the stylet 318 back into the proximal hub chamber 328. A remaining portion of the stylet 318 may remain in the auxiliary passage 320. The end knob 332 is an example of an actuator for the mandrel 330, however, other means for actuating spooling or unspooling via the mandrel 330 may include, among other things, a lateral lever or knob, or a motorized mandrel 330 such as can be triggered via a switch that can include bidirectional and neutral positions.

Figure 9:
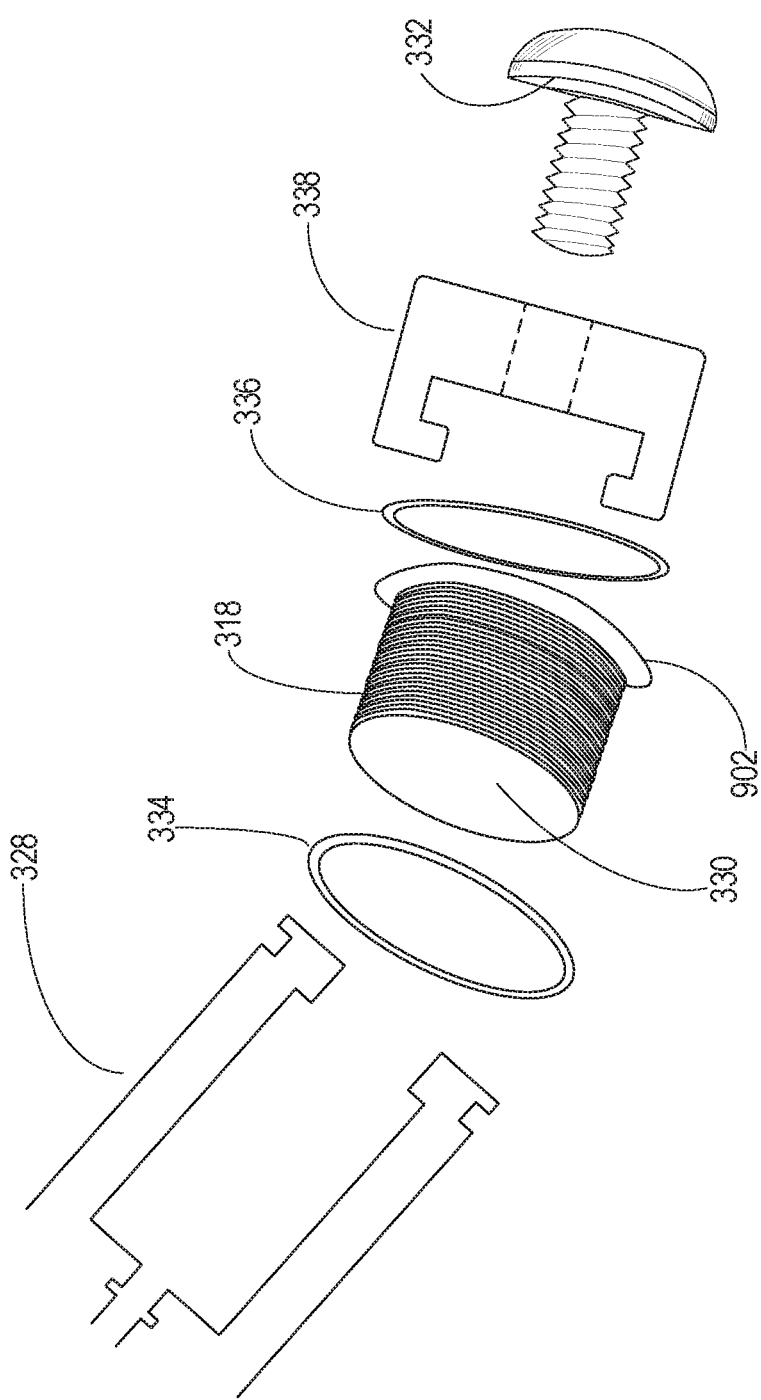
FIG. 9 is an exploded view of the components of the proximal hub chamber of the medical device.

FIG. 9 is an exploded view of components associated with the proximal hub chamber 328 of the medical device. As shown, the proximal hub chamber 328 is exploded with the stylet 318 in a fully retracted position. The proximal hub chamber 328 can include a hub casing 328, a seal 334, a mandrel 330, a stylet 318, a flange 902, a seal 336, cap housing 338, and knob 332. The hub casing 328 may be integrally formed with or otherwise coupled to the tubular body of the debrider 100 and may help house, stabilize, or interconnect certain of the components shown in FIG. 9.

The seal 334 may be joined between the hub casing 328 and the mandrel 330 such as to help inhibit or prevent leakage of irrigation fluid, to contain fluid or gas pressure within the working lumen 308, or to exclude contamination. A portion of the stylet 318 may be tightly wrapped or coiled or spooled around the mandrel 330, such as in an orderly manner that can help inhibit or prevent tangles. A seal 336 may be located between the flange 902 and the cap housing 338. The flange 902 can be configured to permit the mandrel 330 to rotate, such as with the flange 902 being located and rotating within a corresponding receiving groove in the cap housing 338. The knob 332 may include a shaft that can be configured to pass through a corresponding opening in the cap housing 338, such as to permit the shaft to threadably engage or otherwise interconnect with the mandrel 330.

During assembly, a user, a manufacturer, or another assembler may insert the seal 334 into the hub casing 328, insert the stylet 318 into the hub casing 328 through the seal 334, press the mandrel 330 with the stylet 318 tightly spooled upon the mandrel 330 until the top portion of the mandrel 330 is seated against a top portion of the hub casing 328. The top portion of the mandrel 330 may be seated such that the seal 334 allows passage therethrough of the leading end portion of the stylet 318.

The next step in assembling the proximal hub chamber 328 is to insert the seal 336 at a bottom portion of the mandrel 330 and attach cap housing 338 to the bottom portion of the mandrel 330 with the seal 336 in between. The shaft of the knob 332 can be threaded into the mandrel 300 such as via the cap housing 338 and the seal 336.

Figure 10:
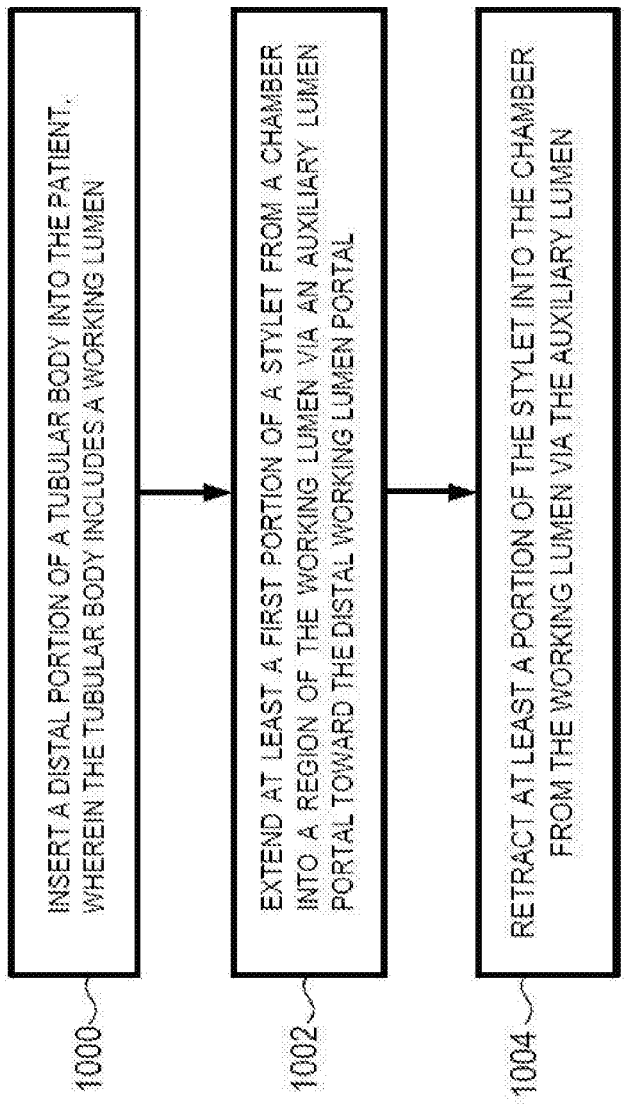
FIG. 10 is a flow chart for an example of a method for operating the retractable stylet declog mechanism.

FIG. 10 is a flow chart for an example of a method for operating the retractable stylet declog mechanism, such as with the debrider 100 of FIG. 1 or other suitable endoscopic or other medical device. The method is but one method for medical therapy of a human patient, other suitable methods can also be used.

At 1000, a user can insert a distal portion of an elongate tubular body 300 into the patient. Such tubular body 300 can include a working lumen 308. The debrider 100 can provide the elongate tubular body 300, such as with a proximal portion 102 and a distal portion 104. The tubular body 300 need not be cylindrical, it can have a different morphology such as with a hexagonal or other polygonal cross-section, or with a smooth or faceted outer surface.

The working lumen 308 may extend between from the proximal working lumen portal 312 at the proximal portion 102 of the tubular body 300 to the distal working lumen portal 202 at the distal portion 104 of the tubular body 300. The working lumen 308 can contain a lateral region that can interface with an auxiliary lumen portal 322 such as at a lateral angle oriented toward the distal end of the tubular body 300.

At 1002, the at least a first portion of a stylet 318 can be extended from the proximal hub chamber 328 into a region of the working lumen 308 via an auxiliary lumen portal 322 toward the distal working lumen portal 202. Extending at least a first portion of the style 318 can be actuated by the user turning the knob 332 in a direction to unspool the stylet 318. Such unspooling can extend a portion of the stylet 318, such as from the proximal hub chamber 328 or the auxiliary passage 320 through the auxiliary lumen portal 322 into the working lumen 308 in a direction that can be oriented or angled toward the distal working lumen portal 202. The user of the debrider 100 can extend at least a portion of the stylet 318 from the chamber 328 by turning the knob 332 and rotating the mandrel 330 so as to extend a portion of the stylet 318 through the working lumen 308 and into the inner tubular member 316 and (optionally) out through the distal cutout inner opening 315 and the distal cutout outer opening 317, together which, when rotationally aligned, can form the distal working lumen portal 202. This can help ream the working lumen 308 or distal working lumen portal 202, or both, such as for declogging.

At 1004, at least a portion of the stylet 318 can be retracted into the proximal hub chamber 328 from the working lumen 308 via the auxiliary lumen portal 322. As an example, when the mandrel 330 spools the stylet 318, the user can rotate the knob 332 to rotate the mandrel 330 in a first direction to unspool the stylet 318 for extending at least a portion of the stylet 318 into the working lumen 308. The user can also rotate the knob 332 in an opposite direction such as to rotate the mandrel 330 in an opposite second direction to spool at least a portion of the stylet 318 for retracting at least a portion of the stylet 318 into the proximal hub chamber 328 from the working lumen 308. During retraction of the stylet 318, an end portion of the stylet 318 can be left positioned within the auxiliary passage 320. The auxiliary lumen portal 322 can include an opening located in between the auxiliary passage 320 and the working lumen 308, such as can be sized, shaped, or otherwise configured to accommodate the cross-sectional width and height of an extendable and retractable stylet 318.

Aspects of the present disclosure are described herein with reference to flowchart illustrations and/or block diagrams of device and method embodiments of the present application. While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A medical device configured for at least partial insertion into a human patient, the medical device comprising:
   an elongate tubular body comprising a proximal portion and a distal portion, the elongate tubular body defining a working lumen extending from a proximal working lumen portal at the proximal portion to a distal working lumen portal at the distal portion;
   an auxiliary passage, interconnected to the working lumen at an auxiliary lumen portal located between the proximal working lumen portal and the distal working lumen portal;
   a stylet, wherein at least a portion of the stylet is configured to extend into the working lumen and toward the distal working lumen portal via the auxiliary lumen portal, and the stylet is configured to retract from the working lumen via the auxiliary lumen portal; and
   a chamber coupled to the auxiliary lumen portal, the chamber including a mandrel, the chamber sized and shaped to house at least a portion of the stylet when retracted from the working lumen, wherein at least a portion of the stylet is configured to be spooled about the mandrel when the portion is in the chamber.

2. The medical device of claim 1, further comprising a knob coupled to the mandrel, the knob being configured to (i) rotate the mandrel in a first direction to unspool the stylet for extending at least a portion of the stylet into the working lumen, and (ii) rotate the mandrel in a second direction, opposite to the first direction, to spool at least a portion of the stylet for retracting at least a portion of the stylet into the chamber from the working lumen.

3. The medical device of claim 2, comprising a first seal between the chamber and the knob.

4. The medical device of claim 1, comprising a second seal between the working lumen and the chamber.

5. The medical device of claim 1, wherein the tubular body comprises an outer tubular member and an inner tubular member, the inner tubular member being coaxial with and rotatable with respect to the outer tubular member, wherein the outer tubular member and the inner tubular member include distal cutout inner openings.

6. The medical device of claim 5, wherein the inner tubular member includes an access opening configured to be aligned, at a specified rotational orientation of the inner tubular member, with the auxiliary lumen portal.

7. The medical device of claim 1, comprising a proximal hub coupled to the tubular body, and wherein the auxiliary lumen portal interfaces with a lateral region of the working lumen, wherein the stylet accesses the working lumen, via the auxiliary lumen portal, at a lateral angle toward the distal portion of the tubular body.

8. A method of medical therapy of a human patient, the method comprising:
    inserting a distal portion of a tubular body into the patient, wherein the tubular body includes a working lumen;
    extending at least a first portion of a stylet from a chamber into a region of the working lumen via an auxiliary lumen portal toward the distal working lumen portal; and
    retracting at least a portion of the stylet into the chamber from the working lumen via the auxiliary lumen into a chamber housing a mandrel about which the portion of the stylet is spooled.

9. The method of claim 8, wherein the extending includes unspooling the stylet and wherein the retracting includes spooling the stylet.

10. The method of claim 8, comprising user-triggering the extending and the retracting via a knob.

11. The method of claim 8, comprising declogging the region using the stylet.

12. The method of claim 11, wherein the declogging includes suctioning.

13. The method of claim 11, wherein the declogging includes irrigating.

14. The method of claim 8, wherein the tubular body includes an outer tubular member and an inner tubular member coaxial to the outer tubular member, and wherein the method further comprises aligning an access opening in the inner tubular member to the auxiliary lumen to allow the extending.

15. The method of claim 8, wherein a second portion of the stylet is positioned in an auxiliary passage between the auxiliary lumen portal and the chamber, and the first portion of the stylet is positioned within the chamber.

16. A medical device configured for at least partial insertion into a human patient, the medical device comprising:
    an elongate tubular body comprising a proximal working lumen portal, a distal working lumen portal, and a working lumen extending from the proximal working lumen portal to the distal working lumen portal;
    an auxiliary passage, interconnected to the working lumen at an auxiliary lumen portal located between the proximal working lumen portal and the distal working lumen portal;
    wherein the tubular body includes an outer tubular member and an inner tubular member, the inner tubular member coaxial with the outer tubular member, wherein the inner tubular member includes an access opening configured to be aligned, at a specified rotational orientation of the inner tubular member, with the auxiliary lumen portal; and
    a stylet, wherein at least a first portion of the stylet is configured to extend into the working lumen and toward the distal working lumen portal via the auxiliary lumen portal when the access opening is aligned therewith, and the stylet is configured to retract from the working lumen via the auxiliary lumen portal and the access opening aligned therewith.

17. The medical device of claim 16, wherein the outer tubular member and the inner tubular member include distal cutout blade openings that are aligned to each other when the access opening is aligned with the auxiliary lumen portal.

* * * * *